United States Patent
Ruegenberg et al.

(10) Patent No.: US 7,454,959 B2
(45) Date of Patent: Nov. 25, 2008

(54) METHOD AND DEVICE FOR PROVIDING DEFINED FLUID FLOW, ESPECIALLY FOR USE IN LIQUID CHROMATOGRAPHY

(75) Inventors: Gervin Ruegenberg, München (DE); Hermann Hochgraeber, Offenberg-Neuhausen (DE)

(73) Assignee: Dionex Softron GmbH, Germering (DE)

( * ) Notice: Subject to any disclaimer, the term of this patent is extended or adjusted under 35 U.S.C. 154(b) by 18 days.

(21) Appl. No.: 10/583,435

(22) PCT Filed: Nov. 23, 2004

(86) PCT No.: PCT/DE2004/002589

§ 371 (c)(1),
(2), (4) Date: Jun. 16, 2006

(87) PCT Pub. No.: WO2005/062036

PCT Pub. Date: Jul. 7, 2005

(65) Prior Publication Data

US 2007/0056357 A1    Mar. 15, 2007

(30) Foreign Application Priority Data

Dec. 23, 2003    (DE) .............................. 103 60 964

(51) Int. Cl.
*G01N 30/00*    (2006.01)
*B01D 53/02*    (2006.01)

(52) U.S. Cl. ..................... 73/61.56; 73/61.57; 96/105
(58) Field of Classification Search ............... 73/23.41, 73/23.42, 61.56, 61.57; 96/105
See application file for complete search history.

(56) References Cited

U.S. PATENT DOCUMENTS 3,271,997 A    9/1966    Home et al.
(Continued)

FOREIGN PATENT DOCUMENTS

DE            199 14 358 A1    10/2000
(Continued)

*Primary Examiner*—Michael Cygan
(74) *Attorney, Agent, or Firm*—Morgan, Lewis & Bockius LLP; David J. Brezner; Victor E. Johnson

(57) ABSTRACT

The invention relates to a method for providing a defined fluid flow, especially for use in liquid chromatography. According to the method, a constant total flow ($f_0$) is subdivided into an internal excess flow ($f_{ie}$) in an excess branch and into an internal working flow ($f_{iw}$) in a working branch. The ratio of subdivision of the internal working flow ($f_{iw}$) and the internal excess flow ($f_{ie}$) depends on the reverse ratio of a fluidic resistance provided in the working branch and a fluidic resistance in the excess branch. The excess branch and the working branch are interlinked at the respective outputs of the two fluidic outputs of the fluidic resistances by a cross-branch. The equalizing flow occurring between the outputs of the fluidic resistances is measured by means of a flow sensor. A desired, external working flow in the further course of the working branch can be fed to a working device, for example a chromatography column mounted downstream of the device. Further down the excess branch a variable fluidic resistance device is arranged. The resistance value of the variable fluidic resistance device is controlled, thereby controlling the equalizing flow in such a manner that the equalizing flow, preferably in the temporal mean, is substantially zero or equals a defined offset value whose amount is small compared to the internal working flow ($f_{iw}$). The invention also relates to a device for carrying out the inventive method.

11 Claims, 3 Drawing Sheets

U.S. PATENT DOCUMENTS

| | | |
|---|---|---|
| 3,282,085 A | 11/1966 | Benson et al. |
| 4,953,388 A | 9/1990 | Barada |
| 5,301,261 A | 4/1994 | Poole et al. |
| 5,547,497 A * | 8/1996 | Klemp et al. ............. 96/104 |
| 5,822,993 A | 10/1998 | Attey |
| 6,627,075 B1 | 9/2003 | Weissgerber et al. |
| 2004/0149011 A1* | 8/2004 | Staphanos ............. 73/23.42 |
| 2005/0092609 A1 | 5/2005 | Gosger et al. |

FOREIGN PATENT DOCUMENTS

| | | |
|---|---|---|
| EP | 0 380 967 A2 | 8/1990 |
| EP | 1 164 340 A1 | 12/2001 |
| JP | 2001-174094 A | 6/2001 |
| WO | WO 97/36560 A | 10/1997 |
| WO | WO 03/066264 A | 8/2003 |

* cited by examiner

METHOD AND DEVICE FOR PROVIDING DEFINED FLUID FLOW, ESPECIALLY FOR USE IN LIQUID CHROMATOGRAPHY

Subject of the invention is a procedure and a device providing a defined fluid flow, especially for liquid chromography.

Analysis technology, especially liquid chromatography (HPLC, High Performance Liquid Chromatography) usually operates based on a constant flow (volume per time unit, volume flow) because it greatly simplifies quantitative analyses. This flow passes through a chromatographic separation column (in short "column"), in which the required separation of materials occurs.

The trend goes to small (CAP-LC) and very small (Nano-LC) volume flows due to the fact that they require only small sampling quantities and achieve a better separation performance. Many applications use a mixture of two or more different solvents. During the analysis, the mixing ratio is often gradually or incrementally changed, which is called the solvent gradient.

As a rule, the use of small volume flows also requires a precisely defined flow. This flow should be adjustable and accurately constant. The latter is made difficult especially by the fact that the counter pressure of the connected column (column pressure) is dependent on the viscosity of the solvent mixture that is present in the column at the time, and can change due to contamination of the column.

It is extremely difficult to create very small volume flows with the required constancy and with a defined adjustable mixing ratio. Added to the very strict requirements regarding the mechanical precision and the density of the components are all kinds of possible dirt effects, which for larger volume flows are negligible.

For this reason, most established procedures use flow splitting. In the first step, a flow that is defined but very much larger than the required flow is created. This makes it easier in comparison to comply with the requirements for constancy and mixing ratio. In classic HPLC, these types of devices are widely used and therefore available commercially. There, a flow splitter is used to divide the supplied flow into a large and a small flow. Only the small flow is used.

Figure 4:
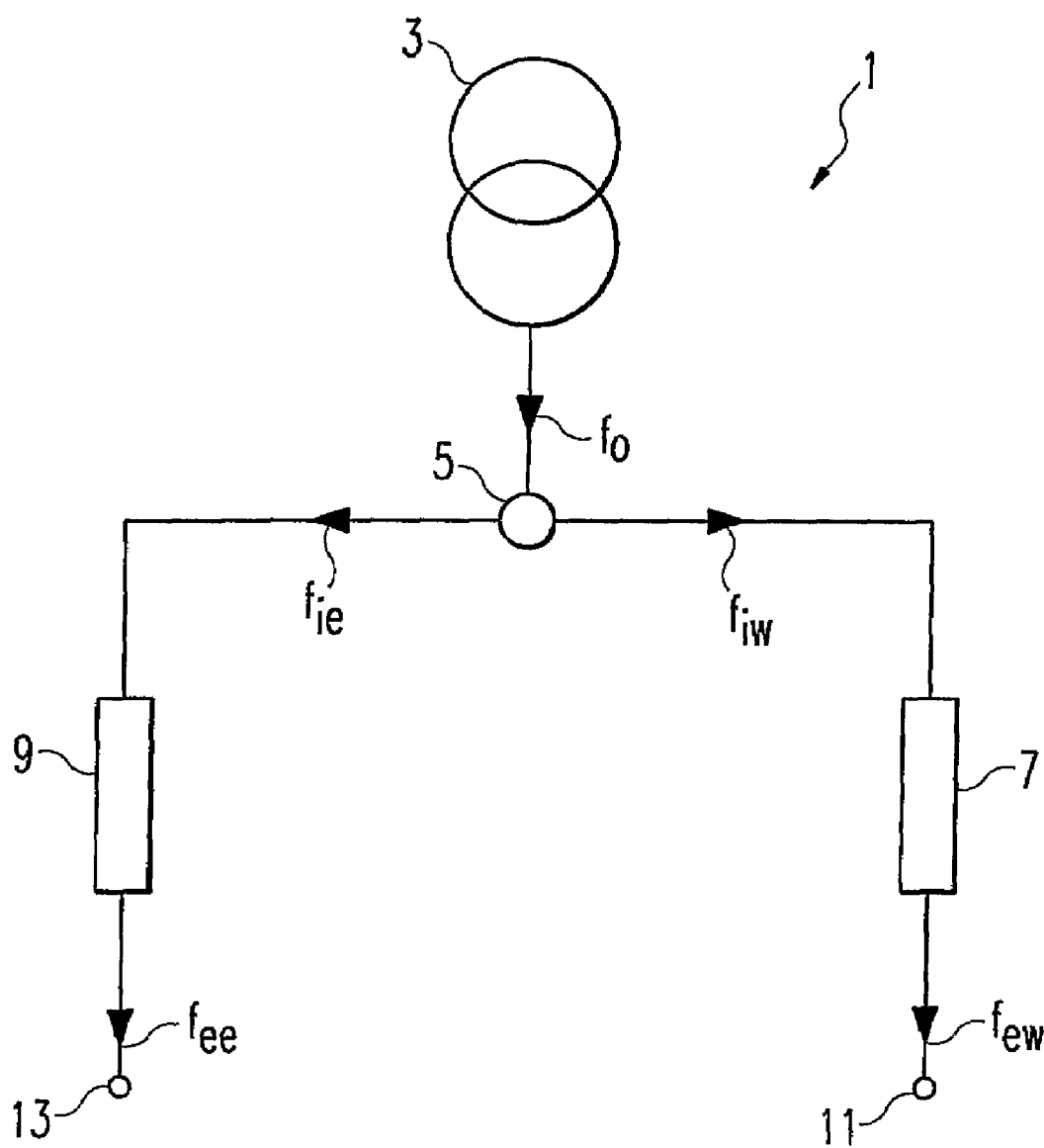

The principle of flow splitting according to the state of the art is illustrated in FIG. 4. The splitting device 1 shown in FIG. 4 for a liquid chromatography device that is not explained in detail here includes a pump 3 for the supply of defined total flow $f_0$ with a defined solvent composition. The pump 3 may contain mechanisms for the proportioning and mixing of different solvents to allow solvent gradients to be created. The total flow $f_0$ supplied by the pump 3 is significantly larger than the desired (external) work flow $f_{ew}$. The splitter further includes a fluidic junction 5, which may be in the shape of a T-junction, and which splits the total flow $f_0$ into an internal work flow $f_{iw}$ und an internal surplus or excess flow $f_{ie}$ as well as a fluidic resistance 7 in the working branch and a fluidic resistance 9 in the excess branch. The split ratio (work flow to excess flow) is determined by the ratio of the resistances. Resistance 7 is usually very much larger than resistance 9, i.e. for an equal drop in pressure the internal work flow $f_{iw}$ only constitutes a small percentage of the excess flow $f_{ie}$.

The internal work flow $f_{iw}$ is also available at the output 11 of the splitter as (external) flow $f_{ew}$. Here is where the rest of the analysis system is connected to the setup. For the pressure ratios, the value of the fluidic resistance of the column (not shown) is especially critical. At output 13 of the flow splitter occurs the (external) excess flow $f_{ee}$, which is equal to the internal excess flow $f_{ie}$ and usually not utilized.

This known procedure has the problem that the split ratio that is actually achieved is not only dependent on resistances 7 and 9 but also on the counter pressure of the column. The fluid resistance of the column is added to the value of resistance 7. This must be considered when dimensioning the resistances.

An additional difficulty is the fact that the fluidic resistances of all components change with the viscosity of the solvents contained in the components. When the solvent composition is constant, all parts are affected equally so that the split ratio remains the same. In solvent gradients, the individual components reflect the change in viscosity with different delays, depending on the throughput rate of the upstream components and the respective component itself. This is the reason why the split ratio does not remain constant during the gradient.

EP-A-0 495 255 describes an improved method. In this case, by tuning the volumes of the two branches corresponding to the split ratio a constant split ratio is achieved, even during a solvent gradient. This method has the drawback that the counter pressure at the output (i.e. the column pressure) continues to strongly affect the split ratio. In the layout of the flow splitter, this counter pressure can only be partially considered since it depends on the viscosity of the solvent as well.

From DE 199 14 358 a method is known where this disadvantage shall be avoided with the use of an active correcting element in one of the two branches. This method uses a working sensor designed to measure the flow in the working branch. Since the sensitivity of flow sensors for such small volume flows is usually strongly dependent on the solvent that is being used, this principle cannot be easily applied to solvent gradients. Therefore, as an alternative solution, it was suggested to detect the pressure in the working as well as in the excess branch, and to use the difference between the two pressures to activate the correcting element.

The disadvantage here is that due to their design, the pressure sensors usually have relatively large inner volumes. Due to the compressibility of the solvents being used and the elasticity of the pressure sensor a flow is moving toward the pressure sensor or moving away from the pressure sensor every time the pressure changes. This decreases or increases the work flow accordingly.

Another problem counter indicating the use of pressure sensors it their achievable accuracy. For technical reasons, the resistances 6 and 7 are designed so that only a small drop in pressure occurs at them. Inaccuracies of the pressure sensors affect the split ratio in correspondence to this pressure drop. Sample: If we assume a pressure drop of 10 bar, then a required flow reproducibility of 0.5% corresponds to an allowable pressure measurement error of 0.05 bar (0.5% of 10 bar).

Since the sensors to be considered measure the total pressure (in relation to the ambient air or absolute) they must have a measuring range of at least 200 bar. A measuring error of 0.05% therefore corresponds to a required accuracy of 0.025%. Such accuracy can only be achieved with great effort.

The invention has therefore the objective to provide a method to supply a defined fluid flow, especially for liquid chromatography, making it possible to generate the work flow with high accuracy independently of the counter pressure at the output without requiring a working sensor in the working branch to detect the pressure and/or the flow. In addition, no pressure sensors should not be used as flow-determining components.

The invention also intends to provide a device for the implementation of this method.

The invention is based on the realization that an external, preferably very small work flow through a working device with sufficient constancy and reproducibility can be achieved by measuring a balance flow between a working branch and an excess branch in a cross-branch, and by adjusting this flow to a value of basically zero or to a preset offset value that is low in comparison to the internal work flow by changing the resistance of an adjustable fluidic resistance device further down the excess branch. This makes the problematic measuring of the external work flow unnecessary.

In a preferred embodiment of the invention, the preset offset value for the balance flow can be selected to be greater than zero, wherein the positive sign indicates the direction of the flow from the working path into the direction of the excess path. This has the advantage that the actual external work flow of the fluid is not corrupted by any influx from the compensation branch as is possible when the balance flow is adjusted to zero, especially with a time median of basically zero, and a fluid with properties that vary over time, like its viscosity, for example.

In an embodiment of the method, the dependency of the signal of the flow sensor on at least one property of the fluid, especially the thermal capacity and thermal conductivity of the fluid, can be corrected by adjusting the balance flow so that the preset offset value for the actually flowing balance flow results. This in turn results in an improved consistency and reproducibility of the external work flow when the composition of the flow varies, especially when a solvent gradient is used in the HPLC.

An easy way to achieve the correction is by linking a correction parameter to the sensor signal, in particular by multiplying a correction factor with the sensor signal.

The values for the correction factor can be stored in a lookup table. The functional dependency of the correction factor on at least one property of the fluid can be stored and utilized for the correction in the same way.

In an embodiment of the procedure according to the invention, the balance flow can be adjusted further down the working path to a preset, relatively high value in comparison to the offset value in order to achieve a temporary reduction of the external work flow. In HPLC, this can be used to achieve a so-called "Peakparking". This is a temporary distinct reduction of the (external) work flow through the column, causing the components that are separated in the column to reach the downstream analysis device at a slower speed and/or with a delay.

In known systems this flow reduction is usually achieved by installing a change-over-valve in the system, which is used to switch to a smaller flow being delivered by a second pump. The additionally components are very costly.

With the system according to the invention this flow reduction can be achieved directly without additional components by temporarily adjusting the balance flow not to a value equal or close to zero but to a significantly higher, positive value.

In an additional embodiment of the procedure according to the invention, the resistance of the adjustable fluidic resistance device to determine the internal work flow and/or external work flow further down the working path can temporarily be adjusted in such manner that a balance flow unequal to zero results, making it possible to determine the internal work flow and/or external work flow to be expected under normal operating conditions based on the signal of the flow sensor.

The adjustable fluidic resistance device for the measurement of the internal work flow in the cross-branch can in particular be shorted and/or be adjusted to a value equal to zero, wherein the cross-branch preferably has a fluidic resistance value equal or close to zero. In this way, the internal work flow can be measured directly. When the balance flow in the cross-branch is adjusted to zero in the normal operating phase of the device, an external flow equal to the measured internal work flow results. If the balance flow is adjusted to a low offset value, especially in order to prevent any reflux of the fluid from the cross-branch into the working branch, then the external flow can be determined during normal operation from the difference between the internal work flow and the balance flow.

In the device according to the invention, the fluidic resistances that determine the split ratio can be such that their fluidic throughput rate is basically the same. This results in the advantage that also in the presence of a time gradient affecting at least one property of the fluid—its composition and therefore its viscosity, for example—the split ratio always remains constant (timewise as well).

A similar effect can be achieved by configuring the fluidic resistances that determine the split ratio in such a way that their fluidic throughput rate is small in comparison to the rate of common solvent gradients. In this case it is safe to assume that the resistances at any time roughly contain a fluid with the same solvent composition.

In another embodiment, the device according to the invention can be designed in such manner that the total fluidic resistance value of the adjustable fluidic resistance device is composed of the resistance of an adjustable, preferably electrically controlled fluidic resistance element and a non-adjustable fluidic resistance element, wherein the fluidic resistance value, especially the value of the non-adjustable fluidic resistance element, is dependent on the viscosity of the solvent being used.

This keeps the required adjustment range for the adjustable fluidic resistance element relatively small, so that this element can be manufactured more easily and at less cost.

Such a device to influence the pressure or flow conditions in a fluidic system can also be used independently of the device or independently of the procedure described in this invention.

Additional embodiments of the invention result from the subclaims.

Figure 1:
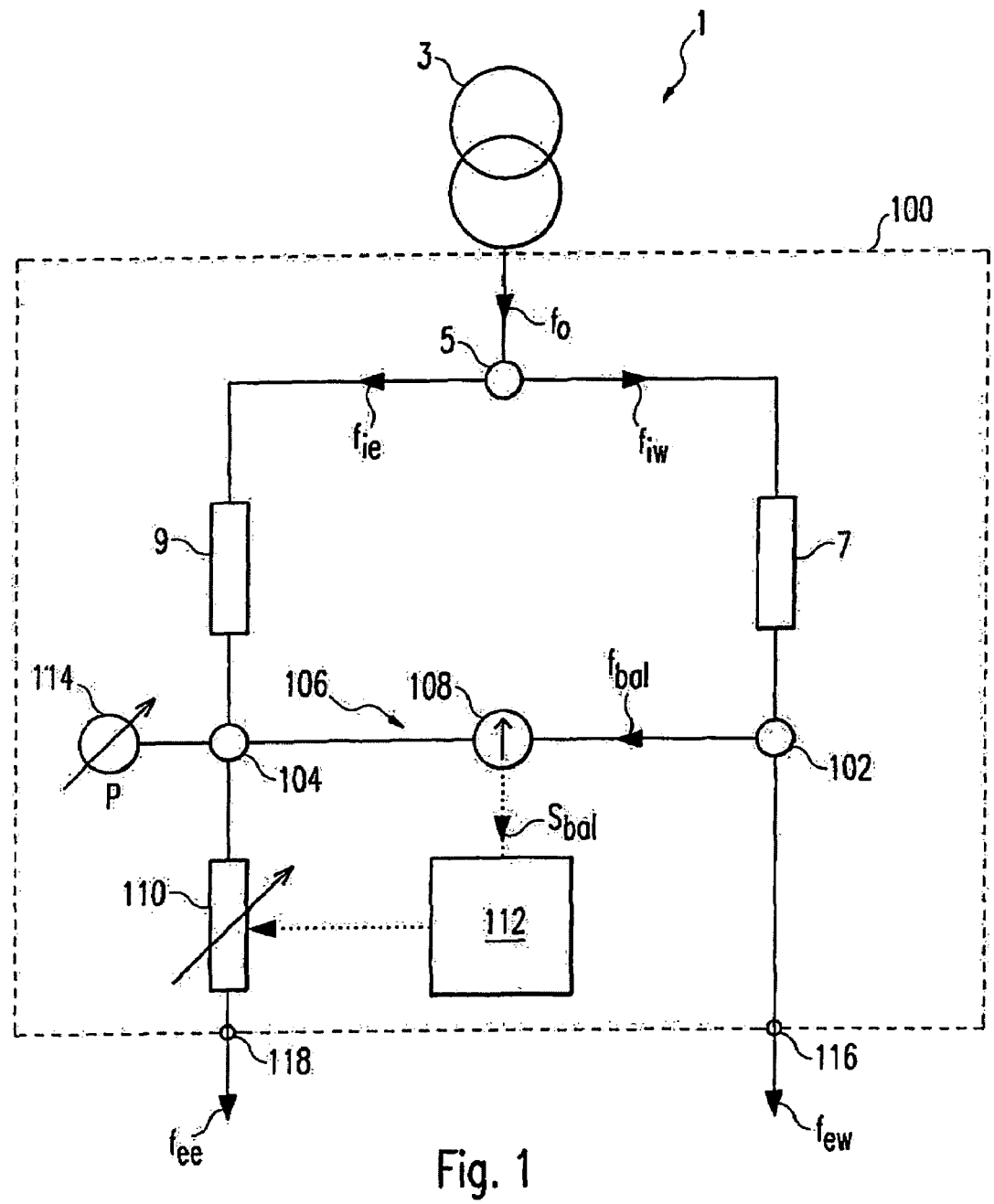
Figures 2A, 2B:
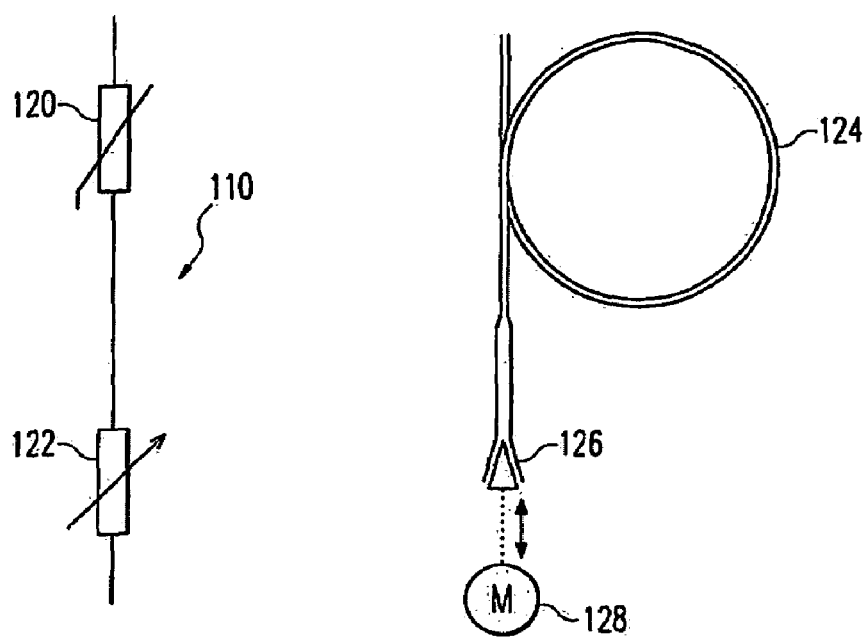
Figure 3:
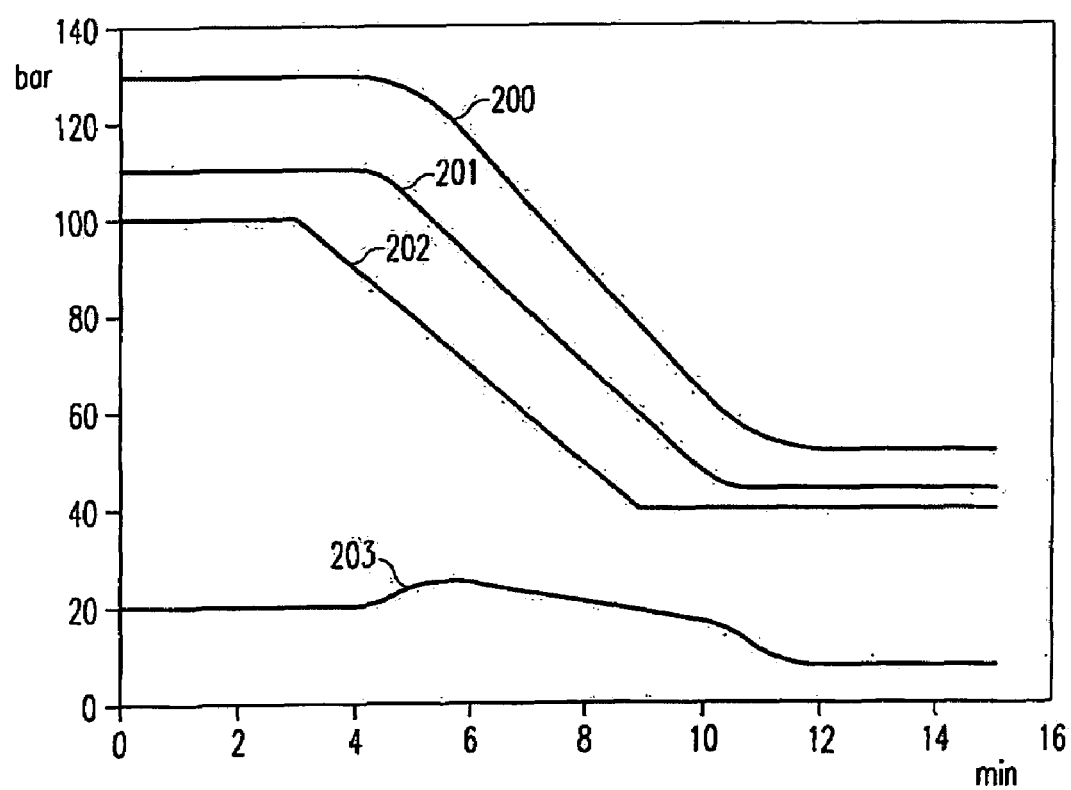

The invention is explained based on a sample embodiment shown in the drawing. The components of the drawing are:

FIG. 1 a schematic view of an analog electrical block diagram of a device according to the invention with a constant-flow pump;

FIG. 2 a schematic view of a controllable, adjustable fluidic resistance device for the device in FIG. 1; in the form of an analog electric diagram (FIG. 2a) and in the form of a principle representation of its implementation (FIG. 2b);

FIG. 3 a diagram to illustrate the viscosity and pressure characteristics of a device according to FIG. 1 with a resistance device per FIG. 2, and FIG. 4 a schematic view of an analog electric block diagram of a device of the state of the art to illustrate the principle of flow splitting.

The device 100 supplying a defined fluid flow, especially for liquid chromatography, shown in FIG. 1 in the form of an analog electric block diagram, being supplied by a constant fluid flow from a pump 1, includes a flow splitter 5, which can be designed as a T-junction, and fluidic resistances 7 or 9 in a working branch or excess branch. This divides the total flow $f_o$ into an internal work flow $f_{iw}$ and an internal excess flow $f_{ie}$, wherein the reverse ratio of these fluidic resistances 7 and 9 determines the split ratio between the internal work flow and the internal excess flow, i.e. the following applies:

$$f_{iw}/f_{ie}=R_9/R_7,$$

wherein $R_7$ and $R_9$ indicate the resistance values of the fluidic resistances 7 and 9.

The device 100 further includes a fluidic junction 102 at the output of the fluidic resistance 7 and a fluidic junction 104 at the output of the fluidic resistance 9. The fluidic junctions 102, 104 again can be configured as simple T-junctions.

Internally, the device 100 has a cross-branch 106 connecting fluidic junctions 102 and 104, and in which a flow sensor 108 is installed, which delivers an output signal $S_{bal}$, which is dependent on the balance flow $f_{bal}$ flowing in the cross-branch 106.

Installed further down the excess branch, i.e. following the applicable branch or output of the fluidic junction 104 is an adjustable fluidic resistance device 110, which, as shown in FIG. 1 can be a simple, adjustable and preferably electrically controllable fluidic resistance, in the form of a controllable throttle valve, for example.

Finally, the device 100 includes a controller 112, which controls the resistance of the adjustable fluidic resistance device 110 depending on the $S_{bal}$-signal of the flow sensor 108. The signal flow is suggested in FIG. 1 by dotted lines.

In addition, an optional pressure sensor 114 can be used at the fluidic junction 9 to detect the pressure at this point.

The output 116 of the device 100 supplies the required external work flow $f_{ew}$, whereby the ratio between the external work flow $f_{ew}$ and the total flow $f_o$ should be kept constant with sufficient accuracy. The excess flow $f_{ee}$ at output 118 of the device 100 is usually not being utilized.

Following is a description of the operating mode of the device in FIG. 1 explained on the sample of HPLC, whereby only the components of the HPLC configuration that are relevant to the invention are being shown:

The configuration—as in known methods—is based on the principle of flow splitting. The pump 3 supplies a defined, preferably constant total flow $f_o$ with the desired, defined solvent composition to the device 100 to whose output 116 the column (not shown) of the chromatography device is connected. The total flow $f_o$ as well as the solvent composition may vary over time.

The flow splitter 5 and the fluidic resistances 7 and 9 in the working path and in the excess path split the total flow $f_o$ into an internal excess flow $f_{ie}$ and a usually much smaller work flow $f_{iw}$.

As explained above, the split ratio is determined by the fluidic resistances 7 and 9 as well as by the pressure decreases at these locations. For a constant ratio of the resistances the split ratio will be constant if the pressure decreases at the resistances 7 and 9 are always equal.

The invention achieves this objective with the help of the cross-branch, which interconnects the outputs of resistors 7 and 9 as well as the fluidic junctions 102 and 104. This connection switches the two resistors 7 and 9 in parallel, so they always exhibit the same pressure loss. This already guarantees a constant split ratio between the internal work flow $f_{iw}$ and the internal excess flow $f_{ie}$. In this case it is being assumed that the pressure drop in the cross-branch is negligible either due to an extremely small balance flow $f_{bal}$ and/or due to an extremely low fluidic resistance in the cross-branch, which is determined by the design of the cross-branch line and the flow sensor 108.

However, depending on the counter pressure at output 116 and the resistance ratios within the total system, there will be a balance flow $f_{bal}$ in the cross-branch, which without additional measures is usually different from zero (positive or negative).

As a result, only the difference between the internal work flow $f_{iw}$ and the balance flow $f_{bal}$ is available at output 116.

In order for the external work flow $f_{ew}$ to be equal to the internal defined work flow $f_{iw}$, the balance flow $f_{bal}$ in the cross-branch must be eliminated.

The invention achieves this objective with the help of the flow sensor 108 in the cross-branch. This sensor detects the balance flow $f_{bal}$ and sends a corresponding signal to the controller 112. The controller changes the adjustable resistor 12 such that the balance flow detected by the flow sensor 108 in the cross-branch generally, especially in the temporal median, becomes zero. This can be accomplished with an electronic controller, as explained below.

If the counter pressure at output 116 changes, which may be caused by contamination of the connected column, temperature changes or a changing solvent viscosity, the immediate result is the balance flow $f_{bal}$ in the cross-branch, which is unequal to zero. This flow is detected by the flow sensor 108 and forwarded to the controller 13, which in turn changes the resistance of the changeable and adjustable resistance device 110 in such fashion that the balance flow $f_{bal}$ goes back to zero. This restores the conditions described above.

As a sample, let's assume that the counter pressure at output 116 increases. The result is a positive balance flow $f_{bal}$, i.e. from the working branch in the direction of the excess branch. In this case, the resistance of resistance device 110 increases until the resistance ratios in both branches are equal again, and the balance flow $f_{bal}$ becomes zero again.

The pressure sensor 114 is used to detect the pressure at the resistance device 110. Since the pressure drop in the cross-branch in the previously described operating mode of the device 100 is zero, this pressure also matches the pressure at the output 116 of the working branch. Although this pressure is not necessary for the control or regulation of the system, it is important in practical applications since it allows deductions regarding the condition (e.g. contamination) of the connected column.

One additional advantage of the configuration according to the invention is that the internal work flow $f_{iw}$ supplied by the fluidic junction 5 and the fluidic resistors 7, 9, which in the previously described operating mode is equal to the external work flow $f_{ew}$, can be checked and measured directly without additional components. This allows the detection of obstructions at the components of the fluidic junction 102 or the fluidic resistors 7,9 as well as any malfunctions of the pump 3. The required measuring step occurs independently of the normal operation of the system and is only used for system checks and failure analysis.

Precondition for the measurement is a constant solvent composition, for which the sensitivity of the flow sensor 108, which is especially dependent on the viscosity of fluid, is known. In order to perform the measurement, the resistance value of the changeable fluidic resistance device 110 is reduced to a value of zero or near zero. This makes the pressure at the fluidic junction 104 or den T-junction, which constitutes this fluidic junction, equal to the outside air pressure. Due to the cross-branch, which has a fluidic restance of zero or near zero, the pressure at the fluidic junction 102 or at the T-junction constituting is junction drops to match the outside air pressure.

The same pressure drop continues to occur at the resistors 6, 7. Since pump 3 supplies a constant total flow 3, all pressures decrease by the same value only. This leaves the internal work flow $f_{iw}$ unchanged.

Due to the fact that there is no more pressure difference between the output 116 and the ambient air, there is no flow due to the high resistance of the connected column, i.e. the external work flow $f_{ew}$ goes to zero. This means that the total internal work flow $f_{iw}$ passes the flow sensor 108, and can therefore be measured in this manner.

In normal operating mode, the internal work flow $f_{iw}$ has the same value as during this measurement. This flow exits completely as external work flow $f_{ew}$ at output 116, because the balance flow $f_{bal}$ is set to zero by the controller in the previously described operating mode. The balance flow $f_{bal}$, which was measured during the measuring step, is therefore to identical to the internal and external flow in normal operating mode.

The described approach means that there is a strong pressure change in the system. Due to unavoidable dead volumes in the system it may take a long time until the pressure conditions in the system stabilize. This can be avoided by not reducing the pressure at the fluidic junction 104 all the way to zero as described before, but only changing it significantly in comparison to normal operating mode, e.g. by reducing it. In this case, the internal work flow $f_{iw}$ cannot be measured directly because a part of this flow is drained through the column connected to output 116.

For the reasons mentioned above, the internal work flow $f_{iw}$ remains constant during this measurement as well, provided the pressure drop in the cross-branch is negligible. The balance flow $f_{bal}$ caused by the pressure change therefore reflects the change of the external work flow $f_{ew}$, which is created by the pressure change. This pressure change is detected by the pressure sensor 114. For this reason the fluidic resistance of the column connected to output 116 can be easily calculated as the ratio of the pressure change to the flow change. Since the resistance of the column doesn't change significantly, the external work flow $f_{ew}$ can be calculated from this pressure and the pressure in normal operating mode.

The fluidic resistors 7 and 9 will be advantageously configured according to EP-A-0 495 255 in such fashion that the ratio of their inside volumes is about the same as the two flows. As a result, both resistors will have the same fluidic throughput time. This has the advantage that a change in the viscosity of the solvent has the same affect on both branches, i.e. the split ratio remains constant in this case as well.

A similar effect can be achieved by holding the inside volume of the fluidic resistors 7, 9 low so that the cycling time of the solvent through the resistors is kept short in comparison to the duration of common solvent gradient. In this case it can be assumed at any time that both resistors 7, 9 contain the same solvent composition, i.e. changes in the viscosity of the solvent affect both resistors equally.

Combining these two measures will achieve that deviations in the throughput or cycling times that can be caused by component tolerances, will not cause any interferences.

It is especially practical to fabricate the fluidic resistors in the form of tubes with a small inner diameter (capillaries), preferably made of fused silica or metal. In these types of capillaries the desired volume and resistance conditions can be easily generated and adjust across a wide range. In addition, these types of capillaries exhibit very good consistency regarding their properties. In contrast to fluidic resistors that are made of porous materials (fritted), there is usually no gradual increase of the fluidic resistor due to contamination.

Since the viscosity of fluids and therefore the fluidic resistance of all components is strongly temperature-dependent, the two resistors 7, 9 that determine the flow should always exhibit the same temperature. Here it is expedient to install these resistors in a joint housing, for example. The absolute temperature of these resistors, however, plays a less important role since both resistors always change by the same factor.

The controller 112 is designed to adjust the flow in the cross-branch to zero or to another preset offset value (compare below). Depending on the type of output signal of the sensor 108 and the necessary control signal for the adjustment of the fluidic resistance device 110 this can bed done in the easiest case through a direct electrical coupling of the signals—via an amplifier, for example—but better via an analog or digital controller. Especially useful is an integrated controller since in this way, the temporal median of the flow in the cross-branch can be brought to zero or kept at a specific value with special precision.

In practice (even when an integrated controller is used), short-term control deviations may lead to a low balance flow fbai that is unequal to zero. This allows small amounts of fluid to get into the working branch from the cross-branch or even from the excess branch. In the event of a solvent gradient, the solvent composition in the cross-branch is usually random, since the solvent located there is replaced only in the event of a control deviation. If, in case of a control deviation, a short-term flow occurs in the cross-branch in the direction of the working branch, then the solvent composition in the working branch will be corrupted by the added solvent from the cross-branch.

That is why it can be useful to adjust the flow in the cross-branch to a median value unequal to zero. If this offset value is selected expediently, on average a low balance flow $f_{bal}$ from the working branch in the direction of the excess branch will be the result. This guarantees that the solvent in the cross-branch always has the same composition as in the working branch. The offset value must be selected so that its impact on the external work flow $f_{ew}$ is negligible. Advantageously, the offset value should be between 0.2% and 5% of the external work flow $f_{ew}$; for example, in a range of about 1%. This is especially advantageous because the signal of the flow sensor 108 is usually solvent-dependent. Since the controller 13 attempts to keep the signal of the sensor constant, the actual balance flow $f_{bal}$ changes depending on the solvent composition. The resulting small corruption of the external work flow $f_{ew}$ does not interfere at such small offset values.

At this point is should be pointed out that within the scope of this description we are also speaking about a control of the flow, when actually the signal of the flow sensor is adjusted to a preset value and when due to the dependency of the flow sensor signal on the thermal capacity and thermal conductivity of the fluid a different flow occurs despite an identical sensor signal at different viscosities.

Since the solvent dependent behaviour as well as each solvent composition are usually known it also possible to correct the generated error in the offset value to a great extent. To do this, the expected solvent composition is calculated from the solvent gradient and the actual throughput time to the flow sensor 108. Based on the known sensitivity characteristics of the sensor, a correction factor for the sensor output signal is now determined. The correction factors could be stored in a lookup table, for example. From the sensor output signal and the correction factor the actual balance flow is then calculated.

Potential errors of this correction affect the external work flow $f_{ew}$ only to a very small extent since the offset value, as explained above, is usually only a small part of the work flow.

The fluidic resistance of the components of the cross-branch have almost no influence on the function of the configuration in normal operating mode since the flow in the cross-branch always has a value of close to zero. The resistance value of the cross-branch, however, should not be too high since this would reduce the sensitivity of the control system.

In order, as described, to be able to use the sensor to measure the internal work flow $f_{iw}$, the fluidic resistance of the cross-branch must be dimensioned as low as possible anyway for the balance flow not to generate a pressure drop in the cross-branch.

In the practical application of chromatographic systems it is sometimes desired to strongly reduce the external work flow $f_{ew}$ through the column connected to the output for a short period of time.

This can be used to achieve that the components that are separated at the column reach the downstream analysis device at a slower rate and/or with a delay. This flow reduction is achieved by installing a change-over valve in the system, which can be used to change over to a smaller flow that is delivered by a second pump. This requires extra cost and effort for the additionally required components.

The configuration in FIG. 1 can be used to achieve an immediate flow reduction without any additional components by adjusting the balance flow $f_{bal}$ temporarily not to a value of zero or near zero, but to a much higher, positive value. This reduces the external work flow $f_{ew}$ supplied from output 116 by the adjusted balance flow $f_{bal}$.

Since the control device 112 can set an exactly defined balance flow, the external work flow $f_{ew}$ can be reduced to an exactly defined, adjustable value.

The device 100 per FIG. 1 therefore offers the advantage that the supplied external work flow $f_{ew}$ at the output 116 is independent of the counter pressure of the equipment connected at that point. Furthermore, the supplied external work flow $f_{ew}$ is also independent from the solvent composition and its changes. Even fast solvent gradients have do not influence the supplied flow. The supplied external work flow $f_{ew}$ always constitutes an exactly defined, constant total flow fo. This applies, apart from the time delay caused by the throughput time, also to the solvent composition. This means that the external work flow $f_{ew}$ can be easily controlled in an exactly defined manner by changing the total flow. In addition there is the possibility to selectively influence the external work flow $f_{ew}$ by setting the balance flow Fbai to unequal zero.

Regarding the components to be used for the configuration, the following additional advantages result:

The flow sensors being used to measure fluid flows are usually based on the measurement of the heat dissipation through the flowing fluid. Since it strongly depends on the properties of each fluid, the sensitivity (scale factor) of such sensors is strongly solvent-dependent. This solvent-dependency leads in the known configuration to a large measuring error.

Since in the operating mode of the device 100 in FIG. 1 described first only the zero point or the direction of the flow needs to be detected, the solvent dependency of the sensor signal doesn't play any role. Non-linearities of the sensor practically also have no effect at all.

If the measurement of the work flow is not required, a flow sensor can be used, which accurately determines the direction and/or the zero point of a flow only. The elaborate calibration of the sensor is not necessary.

If the balance flow $f_{bal}$ in the cross-branch, as described above, is not adjusted to zero but to a (lower) offset value, it is possible to use a flow sensor, which can only detect the amount but not the direction of the flow.

In systems with very small flow rates the use of pressure sensors in the working branch is disadvantageous since they usually exhibit a relatively large dead volume, and based on their design and the compressibility of the fluid amount contained inside of them act like a pressure equalization vessel. Therefore, when the pressure increases, a part of the flow flows into the pressure sensor and when the pressure decreases the pressure sensor supplies an additional flow. An additional pressure sensor connected to the fluidic junction 102 would, for example, falsify the external work flow $f_{ew}$ supplied at the output 116 of the system every time the pressure changes.

The function of the system according to the invention does not require a pressure sensor The pressure of interest at output 116 of the system can usually anyway be detected via the optional pressure sensor 114 with high accuracy.

Since this pressure sensor 114 is installed in the excess branch instead of the working branch, the dead volume of the pressure sensor does not cause any problems. Since the pressure sensor in addition does not have any effect on the accuracy of the flow in the working branch, a simple and cost-efficient design can be used.

The actuator, i.e. the adjustable fluidic resistance device 110 can be implemented in different ways. One obvious solution, for example, is the option to use a variable "bottleneck", whereby the length and/or the cross section of the bottleneck are adjustable.

Critical parameters for the implementation of the actuator are the required working pressure range and the required resolution. The pressure operating at the actuator is the same as the pressure at output 116 of the device (column pressure). It depends on the viscosity of the solvent and the type of chromatographic column. In practice, a pressure range between about 30 and about 400 bar is of interest. For a given column type, the required working range depends on the viscosities of the applicable solvents. For solvent gradients that are of practical interest, the viscosity differences are about 1:3.

For variable solvent compositions, the column pressure (and therefore also the pressure at the actuator) can therefore change depending on the used solvent and/or the mixing ratio at a ratio of up to 1:3.

In an advantageous implementation of the device 100 shown in FIG. 1, where the resistors are configured so that the throughput times for the solvent through the resistors 7 and 9 are generally the same, the solvent composition at both outputs of the flow splitter (e.g. at the junctions 102 and 104) is approximately the same. Therefore, the solvent flowing into the chromatographic column has the same viscosity as the solvent that at the same time flows into the actuator.

This fact can be utilized to dramatically reduce the required working range of the actuator. In doing so, the actuator is implemented as a serial circuit consisting of one fixed and one adjustable fluidic resistance element. The fixed resistance element exhibits a pressure drop, which is somewhat smaller than the pressure drop at the chromatographic column.

Since the fluidic resistance of the fixed resistance element, similar to the resistance of the chromatographic column, changes depending on the viscosity, the working range of the adjustable resistance element of the actuator must only compensate for deviations from this theoretical case and pressure changes due to contamination of the column.

FIG. 2a shows an improved version of the adjustable, changeable fluidic resistance device 110 in the form of electrical symbols as well as a schematic diagram of an implementation option.

The resistance device 110 according FIG. 2 is composed of two resistance elements 120 and 122, wherein the fluidic resistance element 120 is dependent on the viscosity of the solvent that flows through. The fluidic resistance element 122 can be changed by the controller 122.

In the schematic view, the viscosity-dependent part 120 is symbolized by a long, thin capillary 124, whose fluidic resistance value is directly proportional to the viscosity of the fluid. The adjustable part 122 is implemented as an adjustable needle valve 126, whereby the needle can be moved with a motor drive 128 in such manner that the cross section of the passage opening changes.

The resistance elements 120 and 122 can, of course, also be implemented in other ways. For example, instead of a needle valve, the adjustable resistance element 122 could also be realized as a compressible filter element or an elastic sealing element.

The adjustable resistance element 122 does not need to have a linear characteristic. Instead of a needle valve with a motor-controlled needle, a spring-loaded needle can be used, for example. In this casem the adjustable resistance element would be implemented as an adjustable pressure control. Its characteristic corresponds about to the electronic equivalent of an adjustable Z-diode. Such adjustable pressure controller can also be understood as an adjustable resistor with a "bent" characteristic, and is in this description also sub-summarized under the heading of "changeable resistance device". This type of adjustable pressure controller can be used for the implementation of the adjustable resistance device.

FIG. 3 shows for an alterable fluidic resistance device 110 per FIG. 2 the pressure characteristics for a preset time change of the viscosity of the solvent being used. The indicated pressure characteristics result for a configuration according to FIG. 1 with a chromatographic column connected to the output 116.

FIG. 3 shows the pressure conditions for an balance flow fbai of zero. The characteristic 202 is the specific characteristic of the relative viscosity of the used solvent mixture supplied by the pump 3. The starting viscosity is set to equal 100%. Between t=3 min and t=9 min it drops to 40% of the original value since an increasing portion of a solvent with low viscosity is added to the mixture. Such changes in viscosity are typical for the work with solvent gradients.

The chart 200 shows the associated pressure characteristic at the chromatographic column, i.e. at the output 116. Since due to the throughput time through the resistor 7 the viscosity change reaches the column only after a delay, the decreasing viscosity becomes apparent with some delay as well. In addition, the pressure characteristic appears straight since the range with decreasing viscosity occurs only gradually enters the column. Due to the cross-branch the pressure at the resistance device 110, i.e. the sume of the pressures at the resistance elements 120 and 122, is equal to the pressure at the output 116 and therefore also corresponds to the chart 200.

The chart 201 is the pressure drop at the fixed resistance element 120 of the resistance device 110, i.e. at the capillary 124. The time curve approximates the curve 200. The capillary, however, has a shorter throughput time than the column, causing the characteristic to be less straightend or delayed.

Finally, the chart 203 is the difference from the total pressure at the resistance device 110 (chart 200) and the pressure drop at the fixed resistance element 120 at the resistance device (chart 200). This pressure must be built up by the adjustable resistance element of the resistance device 122.

FIG. 3 clearly shows that the chart 203 reaches a maximum of only about 25 bar even though the total pressure at the resistance device 110 (chart 200) is up to 130 bar. This means that the working range of the adjustable resistance element 122 of the resistance device 110 can be much smaller than the total pressure at the resistance deivce.

Theoretically the fixed resistance element 120 of the resistance device could from the beginning be layed out such that its pressure drop exactly matches the one at the column. Then no control would be required, and no cross-branch would be required either. In practice, however, this cannot be realized at reasonable cost. An important reason is that the column gets over time locally contaminated due to use, which not only leads to higher column pressure, but also changes the time characteristic In fluid chromatography, salt is sometimes used as chemical buffers. For high salt concentrations there is the danger that these salts crystallize If this takes place in the resistance device 110, its function could be affected.

This problem can be avoided by equipping the resistance device 110 on the low pressure side with at least two additional connections for rinsing, Through the additional connections, our solvent (e.g. water) can be pumped through the actuator at specific time intervals. This lowers the salt concentration so that the crystallizing will be preveted, and existing salt crystals will be solved and flushed out.

The invention claimed is:

1. Method to supply a defined fluid flow, especially for liquid chromatography,
   a) in which a total flow ($f_o$) is split into an internal excess flow ($f_{ie}$) in an excess branch and an internal work flow ($f_{iw}$) working branch
   b) wherein the split ratio between the internal work flow ($f_{iw}$) and the internal excess flow ($f_{ie}$) is determined by the reverse ratio of a fluidic resistor (7) in the working branch and fluidic resistor (9) in the excess branch, and
   c) where the excess branch and the working branch are interconnected at the outputs of the two fluidic resistors (7, 9) via a cross-branch,
   d) in which the balance flow ($f_{bal}$) occurring between the outputs of the fluidic resistors (7, 9) is measured with a flow sensor (108),
   e) where further down the working branch an external work flow (few can be supplied to an operating device downstream of the device (100),
   f) after which further down the excess branch an adjustable resistance device (11) is installed,
   g) where by control of the resistance value of the adjustable fluidic resistance device (110) the balance flow ($f_{bal}$) is regulated in such manner that the balance flow ($f_{bal}$) is in the temporal median, generally equal to zero or equal to a preset offset value, whose value is small in comparison to the internal work flow ($f_{iw}$),
   wherein the resistance value if the adjustable fluidic resistance device for the determination of the internal work flow ($f_{iw}$) and/or external work flow ($f_{ew}$) further down the working path is temporarily set in such manner that a balance flow ($f_{bal}$) of unequal to zero results, and the internal work flow ($f_{iw}$) expected in normal operating mode and/or the external work flow ($f_{ew}$) is determined from the signal ($S_{vai}$) of the flow sensor (108),
   wherein the adjustable fluidic resistance device (110) is shorted for measuring the internal work flow ($f_{iw}$) in the cross-branch and/or adjusted to a value equal to zero, whereby the cross-branch preferably exhibits a fluidic resistance of equal to or near zero.

2. Method according to claim 1, wherein the preset offset value for the balance flow ($f_{bal}$) is greater than zero, whereby the positive sign indicates a flow from the working path in the direction of the excess path.

3. Method according to claim 1, wherein the dependency of the sensor signal ($S_{bal}$) of the flow sensor (108) on at least one property of the fluid is corrected in such fashion during the adjustment of the balance flow ($f_{bal}$) that the preset offset value for the balance flow ($f_{bal}$) results.

4. Method according to claim 3, wherein for the correcting purposes a correction parameter is linked to the sensor signal ($S_{bal}$).

5. Method according to claim 3, wherein the values for the correction factor are stored in a lookup table, or the functional dependency of the correction factor from at least one property of the fluid is stored.

6. Method according to claim 1, wherein the balance flow ($f_{bal}$) in order to achieve a temporary reduction of the external work flow ($f_{ew}$) further down the working path is adjusted to a preset value that is high in comparison to the offset value.

7. Method according to claim 1, wherein the total fluidic resistance value of the changeable fluidic resistance device (110) is composed of the resistance value of an adjustable, preferably electrically controlled fluidic resistance element (122) and a non-adjustable fluidic resistance element (120), wherein the fluidic resistance value is dependent on the viscosity of the solvent being used.

8. Method according to claim 1, wherein the operating device is a chromatography column.

9. Method according to claim 4, wherein a correction factor is multiplied with the sensor signal ($S_{bal}$).

10. Method according to claim 7, wherein the fluidic resistance value is that of the non-adjustable fluidic resistance element (120).

11. Method to supply a defined fluid flow, especially for liquid chromatography, a) in which a total flow ($f_0$) is split into an internal excess flow ($f_{ie}$) in an excess branch and an internal work flow ($f_{iw}$) in a working branch,
b) wherein the split ratio between the internal work flow ($f_{iw}$) and the internal excess flow ($f_{ie}$) is determined by the reverse ratio of a fluidic resistor (7) in the working branch and fluidic resistor (9) in the excess branch, and
c) where the excess branch and the working branch are interconnected at the outputs of the two fluidic resistors (7, 9) via a cross-branch,
d) in which the balance flow ($f_{bal}$) occurring between the outputs of the fluidic resistors (7, 9) is measured with a flow sensor (108),
e) where further down the working branch an external work flow ($f_{ew}$) can be supplied to an operating device downstream of the device (100),
f) after which further down the excess branch an adjustable resistance device (11) is installed,
g) where by control of the resistance value of the adjustable fluidic resistance device (110) the balance flow ($f_{bal}$) is regulated in such manner that the balance flow ($f_{bal}$) is in the temporal median, generally equal to zero or equal to a preset offset value, whose value is small in comparison to the internal work flow ($f_{iw}$), wherein the dependency of the sensor signal ($S_{bal}$) of the flow sensor (108) on at least one property of the fluid is corrected in such fashion during the adjustment of the balance flow ($f_{bal}$) that the preset offset value for the balance flow ($f_{bal}$) results, wherein the at least one property of the fluid is the thermal conductivity or thermal capacity of the fluid.

* * * * *